US008234912B2

(12) United States Patent
Suarez-Rivera et al.

(10) Patent No.: US 8,234,912 B2
(45) Date of Patent: Aug. 7, 2012

(54) APPARATUS FOR CONTINUOUS MEASUREMENT OF HETEROGENEITY OF GEOMATERIALS

(75) Inventors: Roberto Suarez-Rivera, Salt Lake City, UT (US); Sidney J. Green, Salt Lake City, UT (US); Joel Wesley Martin, Farmington, UT (US); Robert Michael Griffin, Salt Lake City, UT (US)

(73) Assignee: TerraTek Inc., Salt Lake City, UT (US)

( * ) Notice: Subject to any disclaimer, the term of this patent is extended or adjusted under 35 U.S.C. 154(b) by 684 days.

(21) Appl. No.: 12/417,725

(22) Filed: Apr. 3, 2009

(65) Prior Publication Data
US 2009/0260415 A1 Oct. 22, 2009

Related U.S. Application Data

(60) Provisional application No. 61/045,468, filed on Apr. 16, 2008.

(51) Int. Cl.
G01N 3/40 (2006.01)
(52) U.S. Cl. .......... 73/81; 73/78; 73/87; 73/788; 73/856
(58) Field of Classification Search .............. 73/78–87, 73/788, 794, 855, 856, 866.5
See application file for complete search history.

(56) References Cited

U.S. PATENT DOCUMENTS

| 2,217,768 | A |   | 11/1937 | Pearson |             |
|-----------|---|---|---------|---------|-------------|
| 2,801,540 | A | * | 8/1957  | Rondeau | .... 73/150 R |
| 3,058,054 | A | * | 10/1962 | Henderson | ... 324/377 |
| 4,649,737 | A |   | 3/1987  | Jones   |             |
| 4,852,397 | A | * | 8/1989  | Haggag  | ........ 73/82 |
| 4,911,002 | A |   | 3/1990  | Enderlin et al. | |
| 5,076,372 | A |   | 12/1991 | Hellbusch | |
| 5,193,059 | A |   | 3/1993  | Tiab et al. | |
| 5,216,917 | A | * | 6/1993  | Detournay | ..... 73/152.59 |
| 5,323,648 | A | * | 6/1994  | Peltier et al. | .... 73/152.17 |
| H1456     | H | * | 7/1995  | Jero    | ........ 73/842 |
| 5,483,821 | A | * | 1/1996  | Mazzoleni et al. | .... 73/82 |

(Continued)

FOREIGN PATENT DOCUMENTS
JP 11123656 A * 5/1999
(Continued)

OTHER PUBLICATIONS

Suarez-Rivera et al., "Continuous Scratch Testing on Core Allows Effective Calibration of Log-Derived Mechanical Properties for Use in Sanding Prediction Evaluation", TerraTek Publication SPE/ISRM 78157, Oct. 20-23, 2002.*

(Continued)

*Primary Examiner* — David Rogers
(74) *Attorney, Agent, or Firm* — Robert P. Lord; Wayne I. Kanak

(57) ABSTRACT

An apparatus for continuous measurement of a geomaterial is disclosed. The apparatus includes a measuring device and a flat bed operatively coupled to the measuring device. The measuring device includes a moving head configured to move in a longitudinal direction relative to a core section of the geomaterial and a first probe coupled to the moving head and configured to continuously measure a property of the core section. The flat bed includes a load actuator configured to secure the core section during the continuous measurement and axially rotate the core section, as well as a core holder assembly configured to apply confining pressure on a length of the core section.

19 Claims, 7 Drawing Sheets

U.S. PATENT DOCUMENTS

| | | | | | |
|---|---|---|---|---|---|
| 5,490,416 | A | * | 2/1996 | Adler | 73/82 |
| 5,670,711 | A | * | 9/1997 | Detournay et al. | 73/84 |
| 6,105,415 | A | | 8/2000 | Kenney | |
| 7,216,555 | B2 | | 5/2007 | Drummond et al. | |
| 7,287,420 | B2 | * | 10/2007 | Yang et al. | 73/81 |
| 7,412,870 | B2 | * | 8/2008 | Brankov | 73/12.11 |
| 2002/0104371 | A1 | * | 8/2002 | Gitis et al. | 73/81 |
| 2004/0011119 | A1 | * | 1/2004 | Jardret et al. | 73/81 |
| 2005/0172702 | A1 | * | 8/2005 | Gitis et al. | 73/81 |
| 2006/0191327 | A1 | * | 8/2006 | Yang et al. | 73/81 |
| 2006/0288763 | A1 | * | 12/2006 | Tsujii et al. | 73/81 |
| 2008/0141783 | A1 | * | 6/2008 | Wong et al. | 73/844 |

FOREIGN PATENT DOCUMENTS

SU             1492016 A   *   7/1989

OTHER PUBLICATIONS

Rock strength testing device as shown on the Internet at <http://rock.eng.hokudai.ac.jp/uoknor/ok26.htm> from Nov. 1997.*

Dagrain, F., "The TerraTek Scratch Index System: A Tool to Realize Logs of Rock Properties on Core Samples," Aug. 2001 (6 pages).

Richard, T. et al., "The Scratch Test as a Means to Measure Strength of Sedimentary Rocks," SPE/ISRM Eurock '98, Trondheim, Norway, Jul. 1998 (8 pages).

Schei, G. et al., "The Scratch Test: An Attractive Technique for Determining Strength and Elastic Properties of Sedimentary Rocks," SPE Annual Technical Conference and Exhibition, Dallas, Texas, Oct. 2000 (7 pages).

Suarez-Rivera, R. et al., "Continuous Rock Strength Measurements on Core and Neural Network Modeling Result in Significant Improvements in Log-Based Rock Strength Predictions Used to Optimize Completion Design and Improve Prediction of Sanding Potential and Wellbore Stability," SPE Annual Technical Conference and Exhibition, Denver, Colorado, Oct. 2003 (9 pages).

Mitaim, S. et al., "A Novel Apparatus to Determine the Rock Strength Parameters," Proceedings of the 9th National Convention on Civil Engineering, Petchaburi, Thailand, May 2004 (6 pages).

Adachi, J. et al., "Determination of Rock Strength Parameters from Cutting Tests," Proceedings of the 2nd North American Rock Mechanics Symposium: NARMS '96, Quebec, Canada, Jun. 1996 (7 pages).

Coudyzer, C. et al., "Influence of the Back and Side Rack Angles in Rock Cutting," AADE 2005 National Technical Conference and Exhibition, Houston, Texas, Apr. 2005 (12 pages).

Richard, T. et al., "Rock Stength Device: User Notice I, Phenomenological Framework and Test Principle," University of Minnesota, Minneapolis, MN, Apr. 1999 (10 pages).

Stenebraten, Jorn et al., "Evaluation of Shale-Drilling Fluid Compatibility via Scratch Testing," TerraTek Publications, SPE/ISRM Rock Mechanics Conference, Oct. 20-23, 2002, Irving, Texas USA.

Cook, John et al., "Rocks Matter: Ground Truth in Geomechanics,"Oilfield Review, Autumn 2007, pp. 36-55.

Balachandran Balaji et al., "Long-Term Strength Loss of Concrete in Sulfate and Acidic Environments," Center for Innovative Grouting Materials and Technology (CIGMAT), Department of Civil and Environmental Engineering, University of Houston, Houston, Texas USA, Apr. 2004.

Bolger, J.A. et al., "Shock waves in basalt rock generated with high-powered lasers in a confined geometry," Journal of Applied Physics, Nov. 15, 1999, pp. 5461-5466, vol. 86, No. 10.

* cited by examiner

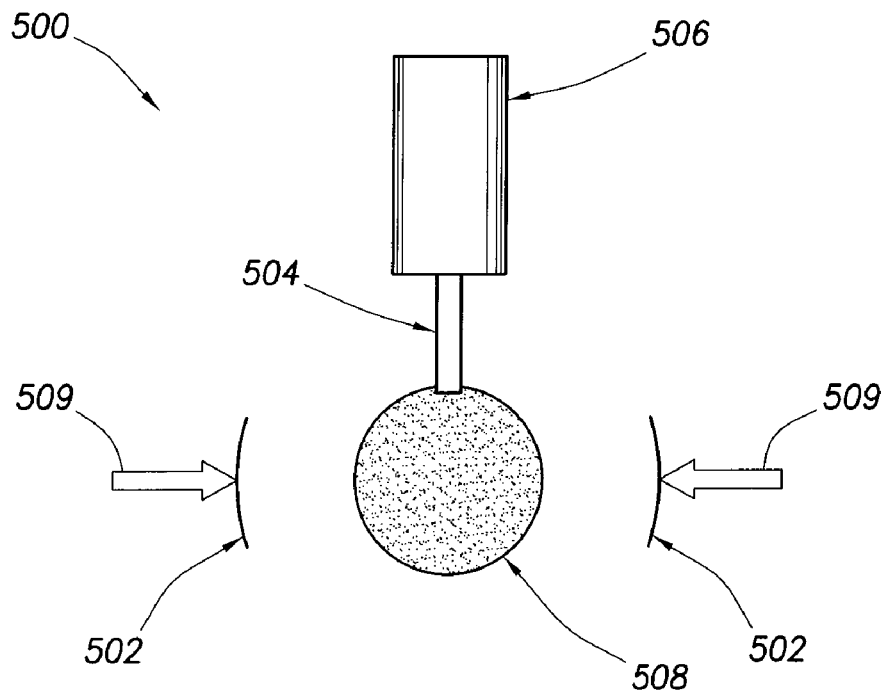
FIG.5
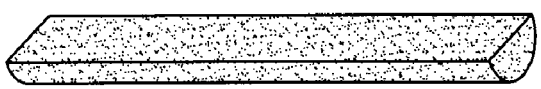
FIG.6.1
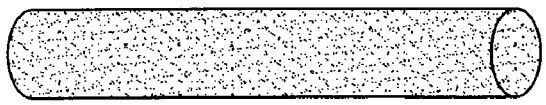
FIG.6.2
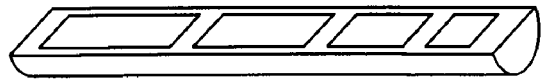
FIG.6.3
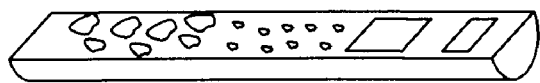
FIG.6.4

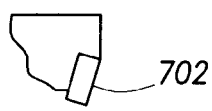
FIG.7.1
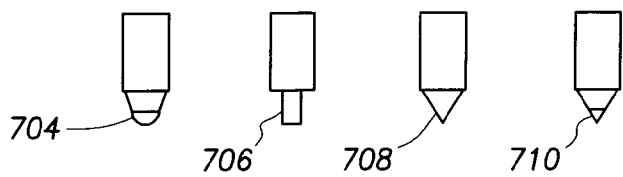
FIG.7.2   FIG.7.3   FIG.7.4   FIG.7.5
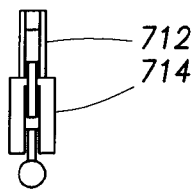
FIG.7.6
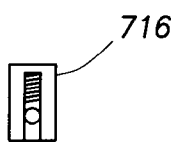
FIG.7.7
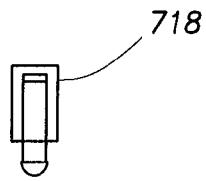
FIG.7.8
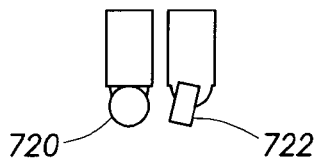
FIG.7.9
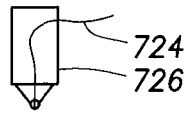
FIG.7.10
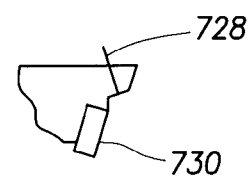
FIG.7.11
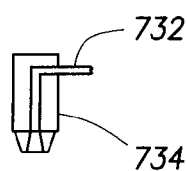
FIG.7.12
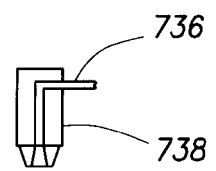
FIG.7.13
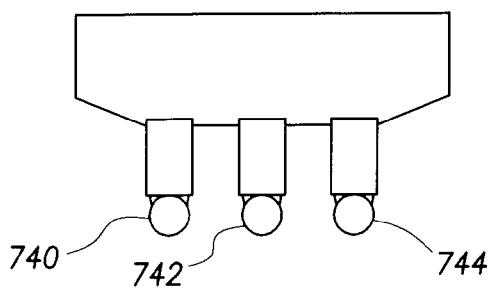
FIG.7.14
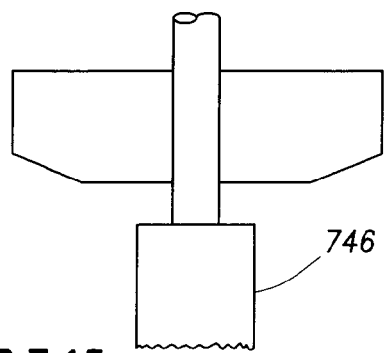
FIG.7.15

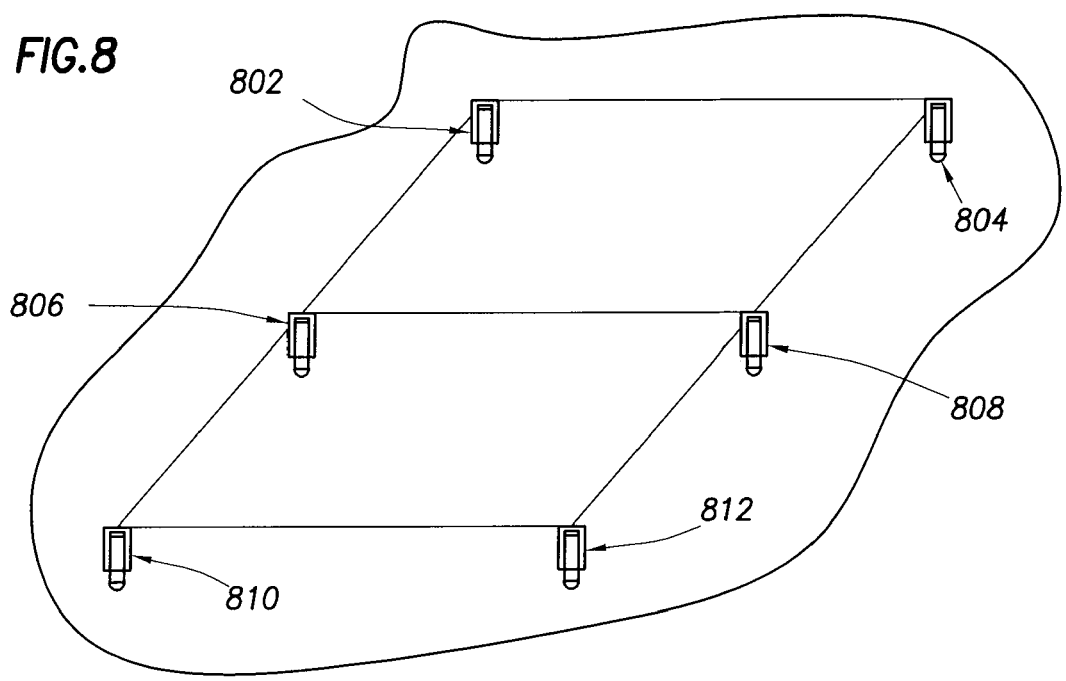
FIG.8
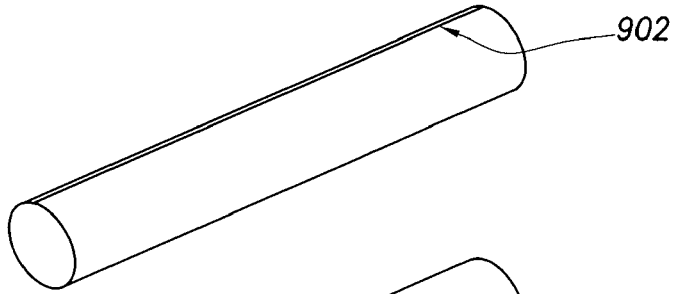
FIG.9.1
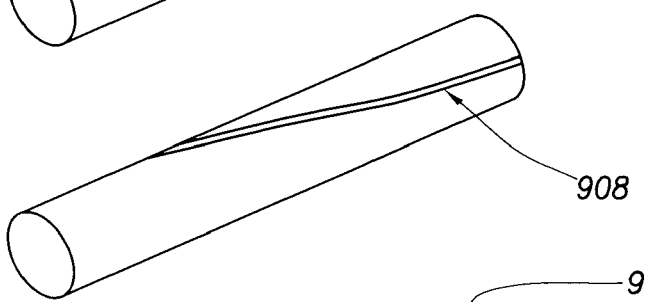
FIG.9.2
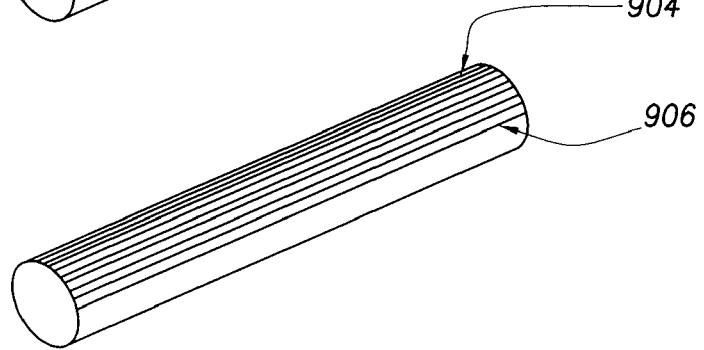
FIG.9.3

APPARATUS FOR CONTINUOUS MEASUREMENT OF HETEROGENEITY OF GEOMATERIALS

CROSS-REFERENCE TO RELATED APPLICATIONS

This application claims priority pursuant to 35 U.S.C. § 119(e) to U.S. Provisional Patent Application No. 61/045,468 entitled "Method and System For Continuous Measurement of Heterogeneity For Scaling From Micro to Large Scale," filed Apr. 16, 2008 in the names of Roberto Suarez-Rivera, Sidney Green, J. Wesley Martin, and Robert Griffin, the disclosure of which is incorporated by reference herein in its entirety.

The present application contains subject matter that may be related to subject matter contained in U.S. patent application Ser. No. 12/417,694, entitled "Continuous Measurement of Heterogeneity of Geomaterials" and filed concurrently with the present application, the entire contents of which are incorporated herein by reference. The referenced application also claims priority to U.S. Provisional Patent Application No. 61/045,468 and has the same inventors and assignee as the present application.

BACKGROUND

Petroleum-related geomaterials are complex materials that are formed by the accumulation of sediments (minerals and fragments from other rocks), are compacted and partially cemented over time, and may be subjected to localized or widespread digenetic alterations that transform their texture and overall composition to their final form. In general, these materials include detrital grains, rock fragments, and a large variety of matrix forming minerals, which may be arranged in various ways, depending on their shapes and size distributions, and in the manner by which they were deposited and altered after deposition. Geomaterials also contain voids (that may be connected or isolated) and pore fluids (water, liquid hydrocarbons or gas). Thus, geomaterials' bulk properties result from their composition and the textural arrangement of their constituents, and include shapes and orientations of pore spaces. As the source of detrital, the conditions of deposition and the post-depositional digenetic alteration changes with time (gradually or abruptly), and the sedimentary column is built up by a sequence of layers whose boundaries may be sharp or transitional, whose properties may be similar or strongly different to each other. As a result, lithologic units are often interbedded with multiple lithofacies, some of which may be further altered diagenetically, or by interaction with living organisms. Geomaterials are thus heterogeneous at many scales (from micro-textural scale to basin scale), and their properties vary vertically and laterally at many scales.

SUMMARY

An apparatus for continuous measurement of a geomaterial is disclosed. The apparatus includes a measuring device and a flat bed operatively coupled to the measuring device. The measuring device includes a moving head configured to move in a longitudinal direction relative to a core section of the geomaterial and a first probe coupled to the moving head and configured to continuously measure a property of the core section. The flat bed includes a load actuator configured to secure the core section during the continuous measurement and axially rotate the core section, as well as a core holder assembly configured to apply confining pressure on a length of the core section.

Other aspects will be apparent from the following description and the appended claims.

BRIEF DESCRIPTION OF DRAWINGS

FIGS. 4 and 5 each illustrate a section view of an apparatus for continuous measurement of a geomaterial in accordance with one or more embodiments.

FIGS. 6.1-6.4 illustrate various core sections in accordance with one or more embodiments.

FIGS. 7.1-7.15 illustrate various probes in accordance with one or more embodiments.

FIG. 8 illustrates a configuration of multiple probes in accordance with one or more embodiments.

FIGS. 9.1-9.3 illustrate examples of continuous measurements of a core section in accordance with one or more embodiments.

DETAILED DESCRIPTION

Figure 1:
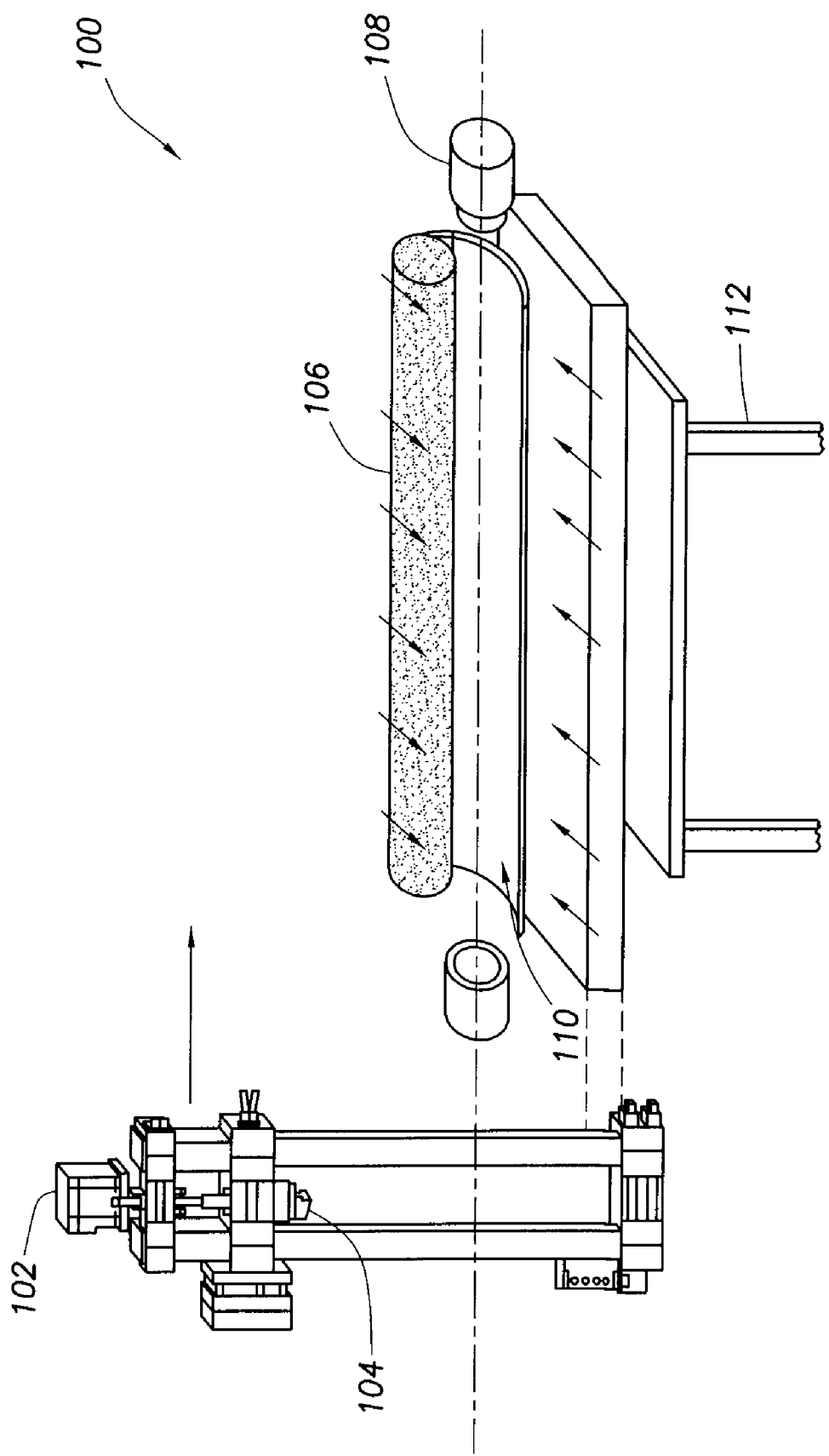
FIG. 1 illustrates the components of an example apparatus for continuous measurement of a geomaterial in accordance with one or more embodiments.

Specific embodiments of continuous measurement of geomaterials will now be described in detail with reference to the accompanying figures. Like elements in the various figures are denoted by like reference numerals for consistency.

In the following detailed description of embodiments of continuous measurement of geomaterials, numerous specific details are set forth in order to provide a more thorough understanding of continuous measurement of geomaterials. However, it will be apparent to one of ordinary skill in the art that continuous measurement of geomaterials may be practiced without these specific details. In other instances, well-known features have not been described in detail to avoid unnecessarily complicating the description.

The embodiments described may be configured to perform continuous measurements of geomaterials from an oilfield. It will be appreciated that the same embodiments may also be used for continuous measurement of geomaterials while performing subsurface operations, such as mining, water retrieval, and acquisition of other underground geomaterials. The embodiments may be used in various applications, including, but not limited to, continuous profiling for mining, civil engineering, or in the oil industry. Further, a device configured to perform continuous measurements may be used in many different situations, including but not limited to conducting measurements on any outcropping, a composite of geomaterials or exposed earthen surface. For example, in one or more embodiments, the device may be applicable to the oil industry to perform measurements while drilling, post-drilling, or on rock samples. In another example, the device may be applicable in the mining industry to perform measurements on tunnel walls for mining excavations. The device may be applicable to the civil engineering industry to perform measurements on extensive surfaces, roads, and compacted areas or in any industry for any outcrop measurement(s).

In one or more embodiments, continuous measurements are material properties measurements such as strength, elasticity, isotropic properties, stress properties, fluid interaction, etc. In one or more embodiments, continuous measurements produce high resolution measurements on the core section being measured; however their resolution may be filtered to a lower resolution. Continuous measurements are not limited to unconfined compressive strength measurement and may be performed on varied shapes and sizes of core sections, or on other samples not in the shape of a core.

Those skilled in the art will appreciate that a geomaterial may correspond to any material on an exposed earthen surface and/or in a subsurface. Examples of a geomaterial include, but are not limited to, composite or man-made materials (e.g., cement, asphalt, etc.), materials on an exposed earthen surface, materials in a rock outcrop, and portions of the subsurface (e.g., portions of a subsurface formation, etc.). Further, a geomaterial, a core, a core section, and a core sample can be of varying shapes and sizes. In one or more embodiments, a geomaterial, a core section, and a core sample may be used interchangeably. In other embodiments, a core section may refer to a sample taken from a geomaterial. In addition, a core sample (i.e., plug) may refer to a sample taken from a core section or a geomaterial.

In general, embodiments of continuous measurement of geomaterials relate to performing a continuous measurement (i.e., "scratch test") along the exposed surface of a core sample, the continuous measurement for determining a heterogeneity of the geomaterial. More specifically, determining heterogeneity of geomaterials may include combining continuous measurement of a geomaterial with, but not limited to, quantitative engineering models and techniques of petrologic, geologic and petrophysical analysis to develop accurate models of material properties for heterogeneous materials. Understanding and measuring heterogeneity of geomaterials requires observations and measurements over multiple scales because the representation of heterogeneity changes with scale. By using continuous measurements of geomaterials, the core heterogeneity may be related to formation characteristics such as rock texture, fractures, interfaces, petrology, and geology, among others.

The analysis of the core samples may occur in a laboratory. Further, the analysis of the core samples may result in a complete evaluation of the heterogeneous geomaterial. In one or more embodiments, the analysis includes performing discrete measurements such as elemental analysis, stress, fluid penetration, and others. These discrete measurements may be used to obtain an adequate representation of the variability of core, log, and/or well heterogeneity. Further, these discrete measurements provide additional measurement values to supplement the continuous measurements. The core sample analysis may be used to accurately characterize unknown areas of heterogeneity. More specifically, the analysis of the core samples may produce information related to reservoir, petrologic, geochemical, mechanical, and other properties of the geomaterial. The analysis may then be used to create models to predict behavior of other areas with similar geologic and petrologic properties.

FIGS. 1-4 illustrate the components of example apparatuses for continuous measurement of a geomaterial in accordance with one or more embodiments. The apparatus (100) illustrated in FIG. 1 includes a moving head (102), a probe (104), a core section (106), a load actuator (108), a core holder assembly (110), a controller (not shown), a user interface (not shown), and a supporting frame (112). Each of these components is described with respect FIG. 1 below. In one or more embodiments, the components of the apparatus (100) are stiffly connected and capable of being utilized in a large number of continuous measurements. In addition, the stiffness of the apparatus (100) may reduce the magnitude of vibration introduced during a continuous measurement. One of ordinary skill in the art will appreciate that the embodiments are not limited to the configuration shown in FIG. 1.

In one or more embodiments, the moving head (102), including the probe (104), is a highly stiff assembly capable of being utilized in a large number of continuous measurements. In addition, the stiffness of the moving head (102) may reduce vibration of the probe (104) introduced during a continuous measurement. The moving head (102) may be configured to traverse the length of the core sample (106) during the scratch test. For example, the moving head (102) may be configured to be pushed and/or pulled by an external device along a structure to accommodate movement of the moving head (102). In another example, the moving head (102) may include an internal drive for moving the moving head (102) longitudinally along a means of traverse. The movement of the moving head (102) may be accommodated in a number of manners including, but not limited to, a rail, a pole, a track, or a set of tracks. In one or more embodiments, the moving head (102) houses wiring or some other device for transferring data collected by the probe (104) to the controller. The movement of the moving head (102) may be controlled by a motor, either located within the moving head (102) or externally. The moving head (102) may also move in a rotational direction, either independently or in conjunction with movement along the length of the core sample (106), as described above.

In one or more embodiments, the moving head (102) is also configured to include the probe (104). The moving head (102) may also be configured to include more than one probe (104). The probe (104) is configured to perform the scratch test (i.e., the continuous measurement). The probe (104) may be configured in a variety of shapes and perform a variety of measurements, as described in more detail with respect to FIGS. 7.1-7.15 below. In one or more embodiments, the moving head (102) is configured to adjust the depth and/or angle of the probe (104) relative to the core section (106). For example, the moving head (102) may adjust the depth and/or angle of the probe (104) relative to the core section (106) at the direction of the controller. Such adjustments of the depth and/or angle of the probe (104) may be made before and/or during a continuous measurement. In one or more embodiments, such adjustments of the depth and/or angle of the probe (104) are made with a high degree of precision. The moving head (102) may also be configured to include a load cell. The load cell may be used to measure horizontal load and/or vertical load placed by the probe (104) on the core section (106). The load cell may be configured to measure the horizontal load and/or vertical load with a high degree of accuracy.

In one or more embodiments, continuous measurements taken by the probe (104) on a core section may include: digital photography (or some other form of a visual representation) and strength measurements to analyze the presence of fractures and interbeds. For example, digital photography provides high resolution evaluation of the texture throughout the core section and strength measurements provide information regarding how strength varies throughout the core section. Combining continuous measurements may provide additional information associated with the presence of fractures and interbeds within the core section. Combining a visual representation of the core section with the strength profile of the core section may be referred to as an overlay. In one or more embodiments, the visual representation is captured during the continuous measurement of the core section. Further, the visual representation may be continually overlaid with the continuous measurement. The combination of continuous measurements listed above is an example of a set of continuous measurements that may be performed. Accordingly, embodiments should not be considered limited to the combination of continuous measurements listed above.

In one or more embodiments, continuous measurements that are performed by the probe (104) are continuous strength measurements to calculate ionic diffusivity. To use continuous strength measurements to calculate ionic diffusivity, the core section is exposed to various brine solutions and continuous strength measurements are performed following the exposure. The continuous strength measurements show the resultant magnitude of chemical interaction in terms of the initial magnitude and depth of penetration for a given time of rock-fluid exposure, thus allowing the calculation of ionic diffusivity.

In one or more embodiments, the core section (106) is a portion of a geomaterial that is subject to the continuous measurement. The core section (106) may be in a variety of forms and sizes, as described in more detail below with respect to FIGS. 6.1-6.4. In one or more embodiments, the size of the core section (106) is suitable for the apparatus (100) to perform a continuous measurement on the core section (106). Further, the continuous measurement performed on the core section (106) may be performed in a variety of manners, as described in more detail below with respect to FIGS. 9.1-9.3.

In one or more embodiments, the load actuator (108) is configured to secure the core section (106) at each end during the continuous measurement. Specifically, the load actuator (108) may secure the core section (106) axially. For example, the load actuator (108) may secure the core section (106) by, but not limited to, (i) penetrating each end of the core section (106) (as with a drill or spike), (ii) using holding devices such as clamps, or (iii) using blunt ends that match up against the ends of the core section (106) and are held in place by a force, such as by the use of hydraulics. In one or more embodiments, the load actuator (108) is also configured to rotate the core section (106) within a range of speeds during some or all of a continuous measurement. The load actuator (108) may be configured to apply axial load or stress to the core section (106) during the continuous measurement. In one or more embodiments, the load actuator (108) is a highly stiff assembly capable of being utilized in a large number of continuous measurements. In addition, the stiffness of the load actuator (108) may reduce vibration of the probe (104) introduced during a continuous measurement.

In one or more embodiments, the core holder assembly (110) is configured to secure the core section (106). Specifically, the core holder assembly (110) may secure the core section (106) by placing pressure (i.e., a confining pressure) at one or more locations along the length of the core section (106). In one or more embodiments, the core assembly (110) is a highly stiff assembly capable of being utilized in a large number of continuous measurements. In addition, the stiffness of the core assembly (110) may reduce vibration of the probe (104) introduced during a continuous measurement. The core holder assembly (110) may apply a confining pressure on the core section (106) using, as shown in the embodiment of FIG. 1, an adjustable ring or cylinder configured to wrap around some or all of the length and/or circumference of the core section (106) and constrict to a point where the desired pressure is applied to the core section (106). In another example, the core holder assembly (110) may apply a confining pressure on the core section (106) using one or more load platens, as described in more detail below with respect to FIG. 5. In another example, the core holder assembly (110) may apply a confining pressure on the core section (106) using a clamping device. In another example, the core holder assembly (110) may also include a flat surface upon which the core section (106) rests without applying added pressure to the core section (106). In this example, the configuration may be utilized when the core section (106) has a flat side, which rests against the load actuator (108), opposite the surface subject to the continuous measurement. Alternatively, when the core section (106) has a curved side opposite the surface subject to the continuous measurement, the core holder assembly (110) may include a portion of a circular tube to assist in securing the core section (106). Those skilled in the art will appreciate that, in one or more embodiments, the core holder assembly (110) may not be attached to the apparatus (100).

In one or more embodiments, the controller is configured to control and coordinate the movements of the moving head (102), the probe (104), the core section (106), the load actuator (108), the core holder assembly (110), and all related equipment. In one or more embodiments, the controller is configured to operate automatically. Further, the controller may be configured to operate with a high degree of precision. The controller may also be configured to collect and interpret data collected from the continuous measurements. In one or more embodiments, the controller determines whether multiple continuous measurements are required for a core section. If the controller determines that multiple continuous measurements should be taken on the core section, the controller may determine what property is measured and the depth and orientation with respect to the core section in the subsequent continuous measurement(s). The controller may also determine a location on the geomaterial to take a subsequent core sample. In one or more embodiments, the controller processes a geomaterial, a core section, or a core sample. Processing may include gamma ray measurements that determine core-to-log depth relationships, identify lithology, and evaluate shaliness and radioactive mineral deposits.

Those skilled in the art will appreciate that continuous measurements may be conducted by the controller at different scales. For example, the continuous measurements may be conducted at, but not limited to, seismic-scale, log-scale, field-scale, well-scale, core-scale, or laboratory sample-scale.

The controller may further be configured to receive data and information from external sources. For example, a user interface (described below) may correspond to an external source. An example of data and information that are included in an external source is a log response, which consist of measurements of properties or behavior (e.g., geologic properties, petrologic properties, reservoir properties, completion properties) of the geomaterial or core section. Log responses may be measured at log-scale (e.g., defined as one measurement every six inches). Geologic properties may include, but are not limited to, stratigraphic divisions, rock classifications, bed boundaries, lithologic descriptions, fracture descriptions, and others. Petrologic properties may include, but are not limited to, textural composition analysis, mineral arrangement analysis, porosity types, mineral compositions, grain size distribution, cementation, organic content, and others. Reservoir properties may include, but are not limited to, porosity permeability, pore fluid saturations, clay bound water, and others. Completion properties may include, but are not limited to, mechanical properties, elastic static and dynamic properties, strength, and others. The measurements collected on geologic properties may be called geologic data; similarly, the measurements collected on petrologic properties may be called petrologic data. Log response measurements may be gathered by a variety of manners including Sonic Scanner (measuring acoustic properties), Elemental Capture Spectroscopy (ECS) (measuring elemental content), Fullbore Formation MicroImager (FMI) (measuring electrical response to produce a borehole image), Modular Formation Dynamics Tester, mud logs, and/or using any other logging tools. Geologic and petrologic data may also be gathered for the core section and subsequently used to determine a relationship with the log response measurements.

Continuing with FIG. 1, another example of data and information from an external source is a cluster analysis of adjacent wells. A more detailed description of cluster analysis is provided below. Once the cluster analysis has been performed, specific core sections may be identified and subsequently obtained when drilling a target well near the adjacent wells. Those skilled in the art will appreciate that a cluster analysis may be performed to verify the core section(s) obtained while drilling. More specifically, the analysis may include conducting log measurements and conducting cluster analysis on the log measurements over the core section. The results of the cluster analysis may be compared with forecasts based on previous measurements at corresponding sections of adjacent wells. If discrepancies exist in the cluster analysis and the previous measurements (e.g., unanticipated faulting), a different core section may be obtained. Other examples of data and information that an external source may provide are discussed more fully following the description for FIG. 9.3 below.

In one or more embodiments, the user interface is configured to allow a user to direct the controller. The user interface may also allow the user to direct the movement of individual components, such as, but not limited to, the moving head (102), the probe (104), the load actuator (108), and the core holder assembly (110). The user-directed movements of individual components may be performed manually (i.e., all movements are controlled interactively by the user) or on a pre-programmed basis. The user interface may be located on the apparatus. Alternatively, the user interface may be located on a computer that is operatively connected to the apparatus.

In one or more embodiments, the supporting frame (112) is configured to support the moving head (102), the probe (104), the core section (106), the load actuator (108), the core holder assembly (110), the controller, the user interface, and all related equipment not expressly shown or described in FIG. 1. The supporting frame (112) may include a flat surface. The supporting frame (112) may also be a self-supporting structure that can be transported and rests on a flat surface (e.g., floor, ground, a lab table, a desktop, etc.) during operation. The bottom of the supporting frame (112) may include wheels, casters, or some similar device to assist in moving the apparatus (100). The wheels, casters, or similar devices may also include locking mechanisms to prevent the apparatus (100) from moving during continuous measurements. The supporting frame (112) may be configured to rest on a floor, ground, or similar surface during operation. Alternatively, the supporting frame (112) may be configured to rest on a lab table, desktop, or similar surface during operation. In this case, the apparatus (100) may be configured for field or remote operations. Further, because of its small size relative to a large-scale apparatus, an apparatus (100) configured for field or remote operations may be limited as to the size of the core sample and as to the number and type of probes used in continuous measurements.

Figure 2:
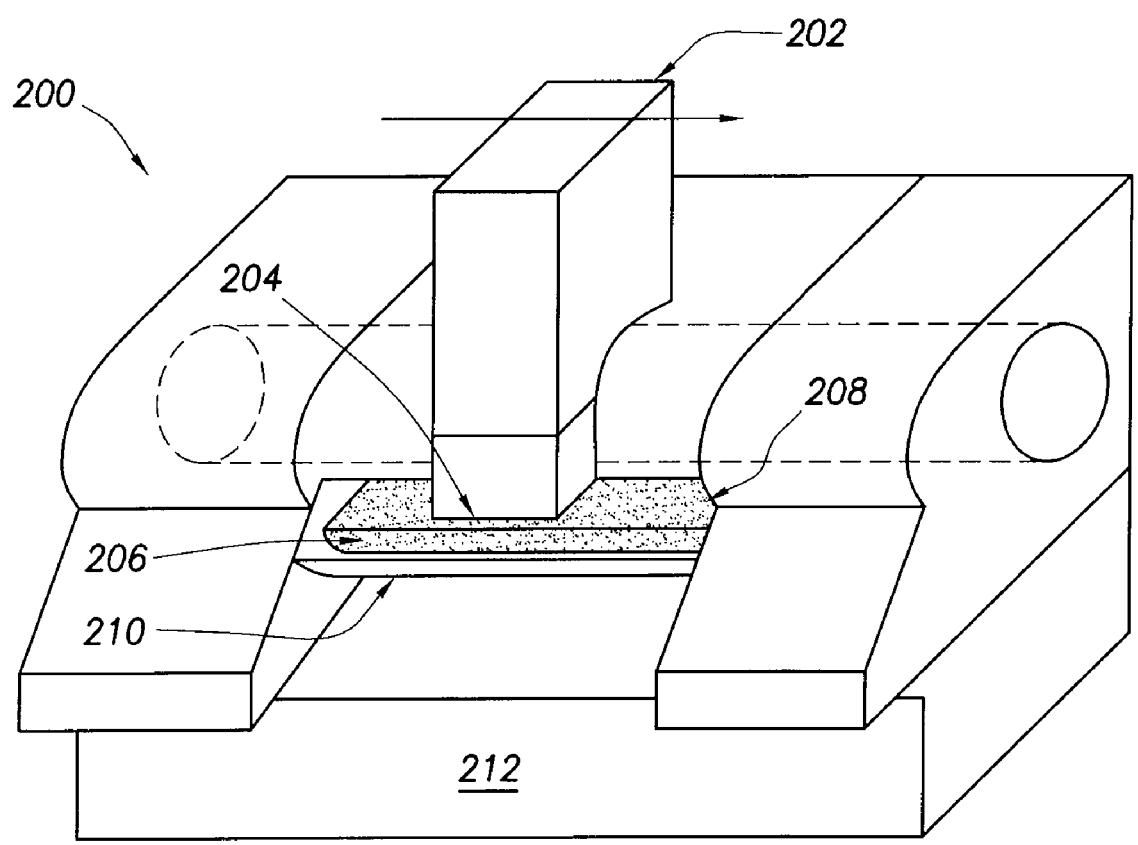
FIGS. 2 and 3 illustrate various examples of the apparatus used for continuous measurement of a geomaterial in accordance with one or more embodiments.

Referring to FIG. 2, a large-scale apparatus (200) is depicted that includes a moving head (202), a probe (204), a load actuator (208), a core holder assembly (210), a controller (not shown), a user interface (not shown), and a supporting frame (212). The moving head (202), a probe (204), a load actuator (208), a core holder assembly (210), a controller (not shown), a user interface (not shown), and a supporting frame (212) may be substantially the same as the corresponding components discussed above with respect to FIG. 1. In addition, in one or more embodiments, the large-scale apparatus (200) includes equipment designed to perform a large number of continuous measurements on a high volume of core samples. The large-scale apparatus (200) may also be capable of performing continuous measurements on larger core samples relative to the core samples discussed in FIG. 1. In addition, the large-scale apparatus (200) may also have the capability of using a larger variety of probes, in number and/or type, compared to the apparatus (100) described above with respect to FIG. 1. For example, the large-scale apparatus (200) may be configured to include a pressure cell, as described below in FIG. 4, where the transportable apparatus described above with respect to FIG. 1 may be unable to accommodate such a configuration. In one or more embodiments, the large-scale apparatus (200) is a highly stiff system capable of being utilized in a large number of continuous measurements. In addition, the stiffness of the large-scale apparatus (200) may reduce the magnitude of vibration introduced during a continuous measurement. One of ordinary skill in the art will appreciate that the embodiments are not limited to the configuration shown in FIG. 2.

Figure 3:
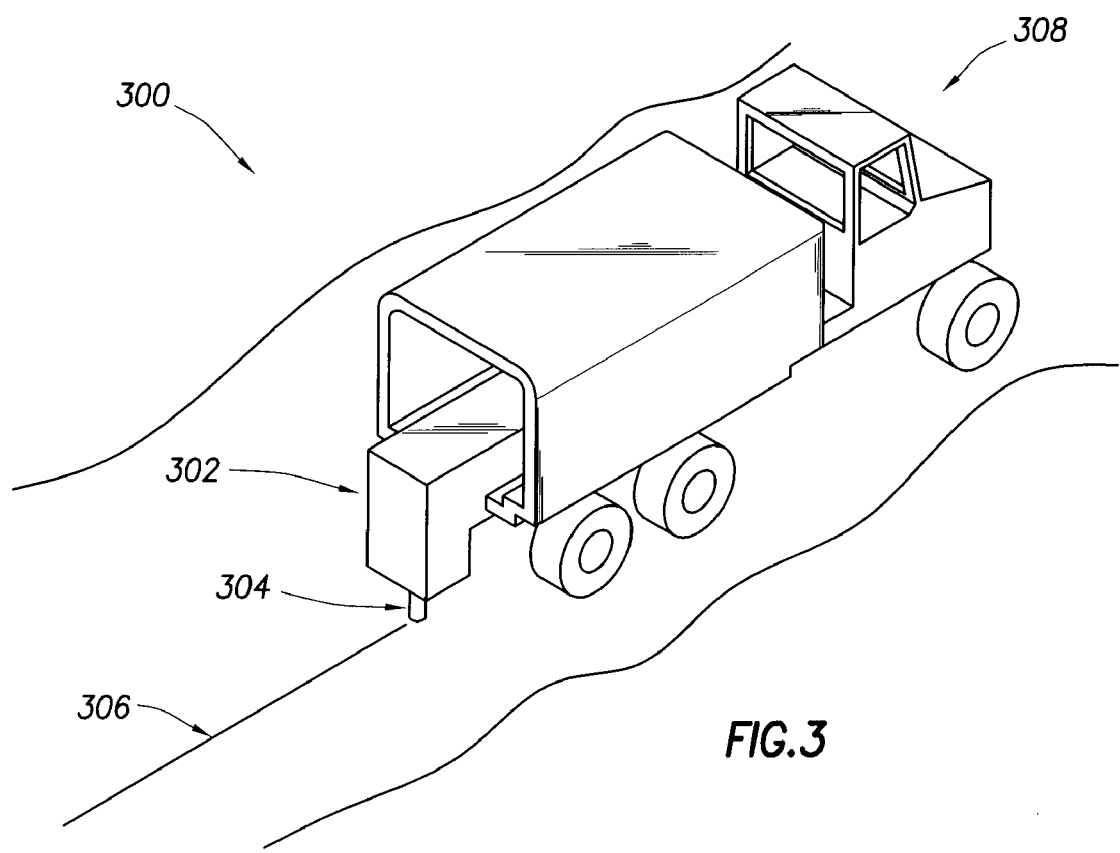

Referring to FIG. 3, a mobile apparatus (300) is depicted that includes a moving head (302), a probe (304), a controller (not shown), and a user interface (not shown). The probe (304), the controller, and the user interface may be substantially the same as the corresponding components discussed above with respect to FIG. 1. In one or more embodiment, the mobile apparatus (300) is positioned on or inside a vehicle (308). The mobile apparatus (300) may be configured to perform a continuous measurement (i.e., scratch test) (306) of a geomaterial on a large surface while the vehicle (308) moves along that surface. In one or more embodiments, the core sample is a geomaterial that has not been removed from an exposed earthen surface, such as road, a plateau, a cavern, or some other exposed earthen environment. Examples of a core sample measured by the mobile apparatus (300) include, but are not limited to, a rock outcropping, a cement roadway, or some other surface. In one or more embodiments, the moving head (302) is configured to move vertically and horizontally independent of the vehicle (308), which acts as a supporting frame. The vehicle (308) may be any mobile device that capable of accommodating the mobile apparatus (300) while the mobile apparatus (300) performs a continuous measurement. Examples of a vehicle (308) include, but are not limited to, a pickup truck, a flat bed truck, a tractor trailer, a van, a trailer in tow of a motor vehicle, and a tow truck. The size of the mobile apparatus (300) may be limited by the carrying capacity and size of the vehicle (308). One of ordinary skill in the art will appreciate that the embodiments are not limited to the configuration shown in FIG. 3. For example, a mobile apparatus (300) may also be configured to be hand-held (not shown) such that a user is capable of transporting the mobile apparatus (300) without requiring the use of a vehicle (308). In this example, the mobile apparatus (300) may be manually positioned by the user on a surface for performing a continuous measurement (306).

Figure 4:
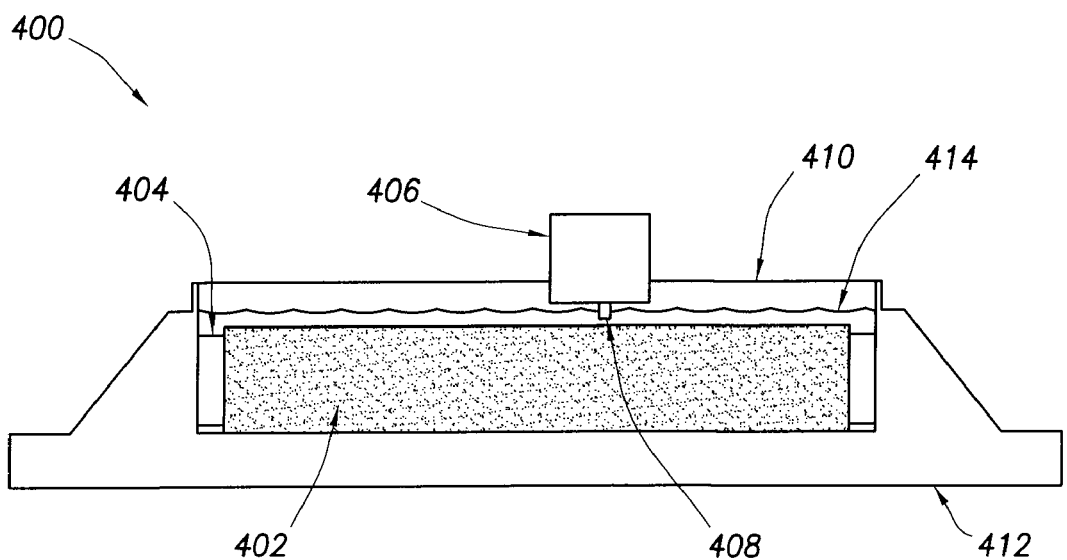

FIG. 4 illustrates a section view of an apparatus (400) for continuous measurement of a geomaterial in accordance with one or more embodiments. The section view in FIG. 4 shows a view depicting the entire path of the moving head (406). In addition to the moving head (406), the view of the apparatus (400) includes a core section (402), a spacer (404), a probe (408), a pressure cell (410), a supporting frame (412), and a fluid (414). The core section (402), moving head (406), probe (408), and the supporting frame (412) may be substantially the same as the corresponding components discussed above with respect to FIGS. 1 and 2. In one or more embodiments, the pressure cell (410) holds the core section (402) as well as the fluid (414) immersing the core section (402). Performing continuous measurements of the core section (402) while immersed in the fluid (414) (or after being immersed in the fluid (414)) may generate data that can be used to evaluate properties and characteristics of the core section (402).

In one or more embodiments, after immersion of the core section (402) in the fluid (414) for a set length of time, repeated continuous strength measurements are conducted until the depth of the invasion zone is located, where the invasion zone is the depth that the fluid has penetrated the core section (402) (i.e., fluid degradation test). In other words, the continuous measurements are conducted at incrementally increased depths in the core section (402) until the results of the continuous measurement are substantially similar to the results of the continuous measurement at the surface of the core section (402) in a dry state.

Continuing with FIG. 4, the fluid (414) may be a variety of fluids, such as a reactant, an inert liquid, an acid, or a brine solution. In one or more embodiments, the fluid (414) is configured to control the environment in which the continuous measurement is performed on the core section (402). In one or more embodiments, the pressure cell (410) is configured to facilitate obtaining continuous measurements of the core section (402) under ambient conditions. Alternatively, the pressure cell (410) may be configured to facilitate obtaining continuous measurements of the core section (402) under in-situ conditions. In one or more embodiments, the pressure cell (410) is configured to control conditions such as pressure, temperature, and humidity. In one or more embodiments, the spacer (404) is configured to help control the environment in the pressure cell (410). The spacer (404) may abut against one or each end of the core section (402). In one or more embodiments, the spacer (404) is a high stiffness reaction spacer. The spacer (404) may provide connectivity between the core section (402) and a load actuator (not shown, but as described above in FIGS. 1 and 2).

FIG. 5 illustrates a section view of an apparatus (500) for continuous measurement of a geomaterial in accordance with one or more embodiments. The section view in FIG. 5 shows a view from the perspective of the base of a core section (508). In addition to the core section (508), the view of the apparatus (500) includes load platens (502), a probe (504), and a moving head (506). The probe (504), moving head (506), and core section (508) may be substantially the same as the corresponding components discussed above with respect to FIGS. 1 and 2 above. A stress (509) may be applied to the load platens (502) against the core section (508) during the continuous measurement. The direction of the stress (509) applied to the core section (508) may vary. For example, the direction of the stress (509) applied to the core section (508) may be perpendicular (i.e., normal) to the surface of the core section (508) to which the force is applied. In one or more embodiments, the load platens (502) are shaped substantially the same as the surface of the core section (508) to which the load platens (502) are applied. For example, the load platens (502) may be curved and configured to encompass the core section (508) with the exception of an opening for allowing the probe (504) to apply substantially continuous pressure while a continuous measurement on the core section (508) is performed. In this example, the curved platens may be flexible to accommodate the shape of the core section (508). In another example, the load platens (502) may be a pair of flat platens, one pair on either side of, and equidistant from, the core section (508). A second pair of load platens (502) may be placed in parallel with the first set of load platens (502), where the second set of load platens (502) are further away from the core section (508). In this case, the space between the first and second pair of load platens (502) on either side of the core section (508) may contain a material (e.g., a semi-compressible solid, etc.) and act as a stress transfer buffer. Those skilled in the art will appreciate that the load platens (502) may also correspond to any suitable combination of curved platens and flat platens. Further, in one or more embodiments, the load platens (502) may be used in conjunction with the load actuator or independently of the load actuator.

FIG. 6.1-6.4 illustrate various core sections in accordance with one or more embodiments. In one or more embodiments, core sections may be samples taken from a geomaterial in a variety of forms such as: full diameter core samples (e.g., FIG. 6.2), slabbed core sections (e.g., FIG. 6.1), drill cuttings, rock fragments, sidewall plugs from field well logs (hereinafter "well logs" or "logs"), or material obtained from any other type of exposed surface (e.g., surfaces exposed during mining operations or other drilling operations). The sample sizes may range from a few grains of a material to large laboratory samples, field outcrops and wellbore surfaces. If the sample to be analyzed is not a whole core section, the sample may be in the form of a slabbed core (e.g., FIG. 6.1), core sections embedded on a supporting substrate (e.g., FIG. 6.3), rock segments embedded on a supporting substrate (e.g., 6.4), side wall samples, rock carvings, or drill cuttings.

In one or more embodiments, the core section (e.g., FIGS. 6.1 and 6.2) may be obtained in a variety of configurations including, but not limited to, a flat slab, half of a circular core (as shown in FIG. 6.1), a circular core (as shown in FIG. 6.2), irregular shapes, or any other shape suitable for continuous measurement. Likewise, the supporting substrate (e.g., FIGS. 6.3 and 6.4) may be obtained in a variety of configurations including, but not limited to, a flat slab, half of a circular core (as shown in FIGS. 6.3 and 6.4), or any other shape suitable for continuous measurement. Core sections are not limited to field wells, and well data is not limited to traditional well logs. Selection of the core sections to analyze may be determined, in part, by data collected from adjacent wells, data collected from the present well, some other factor, or any suitable combination thereof. In one or more embodiments, prior to performing a continuous measurement, the core sample is prepared (i.e., processed) and the combination of continuous measurements to be made on the core section are selected. Processing may include, but is not limited to: depth marking, orientation marking, slabbing, fragmenting, embedding of fragments in a substrate, and surface grinding.

FIGS. 7.1-7.15 illustrate various probes in accordance with one or more embodiments. FIG. 7.1 shows a scratch probe (702), which may be used to perform a scratch test to measure a characteristic of the core sample, such as hardness. In one or more embodiments, the scratch probe (702) comprises one or more diamonds. FIGS. 7.2-7.5 show a series of indentor probes with different heads. In one or more embodiments, the indentor probes measure the hardness of a core sample by applying pressure to the surface of the core sample and measuring the force required to penetrate the core sample. The pressure applied to the surface of the core sample may be a normal force, which is a force applied perpendicular to the surface of the core sample. An indentor probe is configured to measure hardness at a single point on the core sample, but a series of measurements on the core sample may approximate a continuous measurement. FIG. 7.2 shows a probe that includes of a captive sphere (704). FIG. 7.3 shows a probe that includes a cylinder (706). FIG. 7.4 shows a probe that includes a cone (708). FIG. 7.5 shows a probe that includes a diamond (710).

FIG. 7.6 shows a probe that includes a linear variable differential transformer ("LVDT") (712), which is positioned directly above a profilometer tool (714). In one or more embodiments, the probe in FIG. 7.6 is used to measure the topography of the surface of the core section. FIG. 7.7 shows a probe that includes a Schmidt Rebound Probe (716). The Schmidt Rebound Probe (716) may be configured to have an internal mass that is released from within the Schmidt Rebound Probe (716) toward the surface of the core sample using a known amount of energy. The Schmidt Rebound Probe (716) may also be configured to measure the distance that the internal mass bounces off of the surface of the core sample. In one or more embodiments, the probe in FIG. 7.7 is used to measure elasticity of the core section. In one or more embodiments, the Schmidt Rebound Probe (716) probe is configured to measure elasticity at a single point on the core sample, but a series of measurements on the core sample may approximate a continuous measurement. FIG. 7.8 shows a probe that includes an acoustic emission detector (718). In one or more embodiments, the probe in FIG. 7.8 is used to measure acoustic properties (e.g., frequencies) emitted during a continuous measurement. The acoustic emission detector (718) may be used in conjunction with a second probe, such as the probe described in FIG. 7.1 above. In one or more embodiments, measuring acoustic properties emitted during a continuous measurement produces a description of electromagnetic properties associated with the core sample.

FIG. 7.9 shows a wear probe (720) and an abrasion probe (722). In one or more embodiments, the abrasion probe (722) continuously scratches the surface of the core sample, and the wear probe (720) measures the load on the abrasion probe (722) to determine the wear on the abrasion probe (722). In one or more embodiments, measuring wear and abrasion is used to determine the life expectancy of a drill bit. FIG. 7.10 shows fiber optics (724) incorporated into a light beam probe (726). In one or more embodiments, the fiber optics (724) continuously emit light onto the surface of the core sample, and the light beam probe (726) measures the light that is reflected and/or refracted off the surface of the core sample. The light emitted by the fiber optics (724) may be white light, ultraviolet light, infrared light, or any other suitable light. The light beam probe (726) may measure light color, light intensity, some other characteristic of light, or any suitable combination thereof. A test using the fiber optics (724) and the light beam probe (726) may reveal a characteristic or property of the core sample. For example, the fiber optics (724) and light beam probe (726) may reveal or verify a certain type of fluid (e.g., oil) on the surface of the core sample.

FIG. 7.11 shows an atomized liquid distributor (728) that accompanies a probe (730). In one or more embodiments, the probe (730) measures the effect of a fluid emitted by the atomized liquid distributor (728) on the core sample during a continuous measurement. FIG. 7.12 shows a vacuum (732) incorporated into a vacuum probe (734). In one or more embodiments, the vacuum (732) extracts and measures fluid in a pore space in the core sample that is traversed by the vacuum probe (734). FIG. 7.13 shows a pulse injector (736) incorporated into a probe (738), which measures the pressure of the pulses emitted by the pulse injector (736) over time to obtain a pulse permeability measurement. In one or more embodiments, the pulse injector (736) continuously emits pulses toward the surface of the core sample, and the pulse permeability probe (738) measures the pressure of the pulses over time to determine a resulting pulse permeability.

FIG. 7.14 shows a configuration where multiple probes (e.g., probe A (740), probe B (742), and probe C (744)) are aligned on the same measuring tool. The three probes shown in FIG. 7.14 (probe A (740), probe B (742), and probe C (744)) may be aligned in a number of configurations, including but not limited to in series, in parallel, at an offsetting angle, with probe A (740) at the leading edge of the continuous measurement, with probe B (742) at the leading edge of the continuous measurement, with probe C (744) at the leading edge of the continuous measurement, or any other suitable configuration or combination thereof. In addition, probe A (740), probe B (742), and probe C (744) may measure the same or different properties of the core sample. Probe A (740), probe B (742), and probe C (744) may be positioned at different heights relative to the surface of the core sample. In one or more embodiments, the measuring tool may include as many probes as can practically be accommodated during a continuous measurement of a core sample. In one or more embodiments, probe A (740), probe B (742), and probe C (744) measure the same property of a core sample at different depths, providing information to create a three-dimensional image of the core sample. The three-dimensional image of the core sample may identify non-homogeneous features of the core sample, including strike and dipping features of the core sample properties and fractures or bed interfaces of the core sample.

Continuing with FIG. 7.14, the multiple probes (e.g., probe A (740), probe B (742), and probe C (744)) may be used to generate a continuous profile of the strike and dip (and associated direction) of rock fabric for the core sample, including beds and fractures where the fractures are either natural or induced. For example, the multiple probes (e.g., probe A (740), probe B (742), and probe C (744)) may be used to continuously measure the strength of core samples from tight gas shales, which are often layered and strongly heterogeneous, at three different depths to obtain a profile of the dip and dip direction of the shale beds. In this example, a prediction of the effective mechanical properties of tight gas shales may be derived by analyzing the dip and dip direction of the shale beds. Specifically, the analysis of dip and dip direction may allow for the prediction of facture density and fracture orientation of the tight gas shales at a cluster level, which may be used to determine the fracture potential of each cluster unit during hydraulic fracturing.

FIG. 7.15 shows a drill bit probe (746). In one or more embodiments, the drill bit probe (746) is configured to take a sample of the core section. During the rotation of the drill bit probe (746), measurements may be taken of associated characteristics, such as torque of the drill bit probe (746), to characterize one or more properties of the samples of the core section. In one or more embodiments, the sample taken by the drill bit probe (746) may be further tested in a laboratory.

FIG. 8 shows a grid of probes, which includes an acoustic transmission probe (802) and a number of acoustic receiving probes (e.g., 804, 806, 808, 810, and 812). In one or more embodiments, the positioning of the probes (e.g., 802, 804, 806, 808, 810, and 812) is configured in such a way that the distances between each of the probes (e.g., 802, 804, 806, 808, 810, and 812) is known. In one or more embodiments, the acoustic transmission probe (802) is configured to send a pulse, and the acoustic receiving probes (e.g., 804, 806, 808, 810, and 812) are configured to measure the velocity of the pulse. The acoustic receiving probes (e.g., 804, 806, 808, 810, and 812) may be configured to receive pulses that are parallel, perpendicular, and oblique in relation to the surface of the core section. In one or more embodiments, the acoustic transmission probe (802) is configured to send a pulse against the core sample, move a small distance (e.g., one millimeter), and send another pulse against the core section. The acoustic receiving probes (e.g., 804, 806, 808, 810, and 812) may also be configured to move along with the acoustic transmission probe (802). In one or more embodiments, the acoustic receiving probes (e.g., 804, 806, 808, 810, and 812) are configured to measure. compressional and/or shear waves. The measurements of the acoustic receiving probes (e.g., 804, 806, 808, 810, and 812) may be compared with larger-scale acoustic tests (e.g., seismic analysis on the formation containing the geomaterial, sonic logging) to determine, for example, if the degree of heterogeneity of the core sample as recorded by the acoustic receiving probes (e.g., 804, 806, 808, 810, and 812) is substantially reflected in the larger-scale acoustic tests. Significant discrepancies between the two acoustic tests may indicate that other continuous measurements of the core sample should be performed.

Alternatively, in one or more embodiments, probe (802) is one of the probes described with respect to FIGS. 7.1-7.7 and FIGS. 7.9-7.15. In addition, the remaining probes (e.g., 804, 806, 808, 810, and 812) may be the acoustic emission probe as described with respect to FIG. 7.8 above. In such embodiments, the acoustic emission probes (e.g., 804, 806, 808, 810, and 812) are configured to measure the acoustics emitted while the probe (802) performs the continuous measurement on the core sample. As described above, information collected by the acoustic emission probes (e.g., 804, 806, 808, 810, and 812) may produce a description of electromagnetic properties associated with the core section.

FIGS. 9.1-9.3 illustrate examples of continuous measurements of a core section in accordance with one or more embodiments. In one or more embodiments, the continuous measurement along a core section is taken in a single longitudinal line (902), as shown in FIG. 9.1. The continuous measurement taken along a single longitudinal line (902) may include a number of passes with a probe, increasing the depth of the problem in the core sample with each pass. For example, the depth of penetration of a fluid may be determined by: performing a continuous measurement of the core sample when the core sample is dry; immersing the core sample in a fluid for a period of time; removing the core sample from the fluid; and performing longitudinal continuous measurements of the altered core sample at increasing depths until the results of the first continuous measurement are substantially the same as the measurement of the altered core sample. In this example, the depth at which the measurements of the altered core sample are substantially the same as the measurements of the dry core sample indicates the penetration of the liquid into the core sample.

In one or more embodiments, the continuous measurement along a core section is taken in a helical line (908), as shown in FIG. 9.2. The continuous measurement taken along a helical line (908) may include a number of passes with a probe, using an increased depth into the core sample with each pass. The depth of penetration of a fluid may also be determined, as described above for FIG. 9.1, by performing the continuous measurements along a helical line (908). The helical path of the continuous measurement may be determined by rotating the core section during the continuous measurement, by rotating the probe during the continuous measurement, or a combination of rotating the core section and the probe. In one or more embodiments, performing a continuous measurement in a helical line generates information regarding the anisotropic properties of the core sample.

In one or more embodiments, as shown in FIG. 9.3., a continuous measurement (904) is taken along a core section, the core section is rotated, and another continuous measurement (906) is taken along the core section in parallel to the first continuous measurement. The process may be repeated for any number of continuous measurements, including up until the continuous measurements have substantially traversed the entire surface of the core section. The parallel continuous measurements may be longitudinal or helical. In addition, a continuous measurement along a longitudinal or helical line may include more than one pass at increasing depths before the core section is rotated. In one or more embodiments, performing a series of continuous measurements in parallel along the surface of the core sample generates information regarding the radial and longitudinal distribution of properties of the core sample. Continuous measurements may be conducted along any direction in relation to bedding orientation, fracture orientation, or any other textural feature, including radial, axial or transverse orientations. In one or more embodiments, continuous measurements may also measure volumetric heterogeneity through continuous measurements and removal of material (e.g., on a cylindrical sample by scratching along a helicoidal path) until the majority of the material is removed and properties as a function of radial distance from the original surface are measured (with increasing depth of penetration). Topographic reconstructions of the continuous measurements provide a high resolution visualization of variability in strength for the entire volume of the sample. Continuous measurements of volumetric heterogeneity may be used for randomly heterogeneous media, including but not limited to carbonate reservoirs.

Those skilled in the art will appreciate that the previous examples described with respect to FIGS. 1-9.3 are provided for representative purposes only and accordingly should not be construed as limiting the scope of continuous measurement of geomaterials.

In one or more embodiments, the continuous measurements of a geomaterial taken by the apparatus are used in conjunction with other data related to the geomaterial in order to discover or isolate properties of the geomaterial. For example, an overlay may be created using the continuous measurements and log responses. The results of the continuous measurements may be made visually apparent by overlaying digital photographs of the sample with the continuous measurements. More specifically, the overlay is created by superimposing the continuous measurements over a photograph of the core section being measured, where the superimposed measurement value is directly on top of the point on the sample being measured. If the sample being measured is not a core section but is instead another type of exposed surface, the overlay may be created using a digital photograph of the exposed surface. In one or more embodiments, if the continuous measurements are at core scale and the cluster analysis is at log scale, then one or more relationships may be established between the two scales, allowing for core-log integration. In one or more embodiments, the overlay makes the results of the continuous measurements visually apparent. In this example, the overlay allows for direct observations of the relationship between the continuous measurements and the texture, composition and material properties. For example, measurements of unconfined compressive strength may be overlaid with a digital photograph of a sample to evaluate changes in mineral content, changes in lithological boundaries, quantitative and qualitative geological observations, changes in fracture density, boundaries of interbeds and mineral filled fractures, and variability of mineral content and rock fabric. In one or more embodiments, a three cutter head (i.e., three probes, as described in FIG. 7.14) may be used to measure continuous strength profiles allowing the fracture and bedding orientation to be analyzed. The examples of overlays listed above are not meant to be inclusive and those skilled in the art will appreciate that the overlays may take other forms. Analysis of the variability in material properties assists in defining the heterogeneity of the core section and may assist with identifying locations to select additional samples.

As a further example, in one or more embodiments, an overlay is created by integrating continuous measurements with geologic and petrologic observations and description. Geologic and petrologic observations and descriptions may include quantitative or qualitative data. Examples of geologic and petrologic observations and descriptions include, but are not limited to, structural observations, rock and mineral specific observations, and fracture descriptions. The overlay may also be integrated with a visual representation of the core section. The visual representation of the core section may be integrated with the overlay by adding an additional code at the bottom of the overlay that details the geologic and petrologic data. The code may be implemented with colors or numbers for graphical evaluation. The integration may reveal further details regarding visual observations of textural changes, composition changes and corresponding changes in material properties. Integrating the visually apparent results with geologic/petrologic observations and descriptions allows for further evaluation of the sample for consistency through direct visual observation of texture, composition, and material properties. The integration may be used to develop core to log scaling relationships and for integrating the analysis to log scale heterogeneity, based on a particular well.

In one or more embodiments, continuous measurements may be used for further evaluation after integration of geologic and petrologic observations and description, such as: evaluation to measure fracture characteristics (e.g., fracture density and fracture orientation (dip and azimuth)) to compare with corresponding core fracture and log fracture analysis; analyzing the location, frequency and strength of interbeds; analyzing the relationship between specific rock types and strength; and evaluating the thickness of finely-resolved thin beds for sedimentologic analysis. Further, continuous measurements may be filtered to log resolution (i.e., two measurement points per foot) to create an additional representation of the measurement to be used in the overlay. The additional representation of the measurement used in the overlay may be used to identify locations within the core from which to obtain selected core samples.

In one or more embodiments, an integrated overlay, as described above, is analyzed to identify locations within the core from which to obtain selected core samples. In one or more embodiments, the integrated overlay is analyzed to identify selected core samples (i.e., additional samples) that may undergo additional analysis, including continuous measurements, to more accurately characterize the properties of the homogeneous medium or the properties of the various constituents of the heterogeneous medium. Those skilled in the art will appreciate that the selected core samples may be laboratory samples. The core samples may be selected using the integrated overlays and statistical analysis (e.g., cluster analysis, analysis of variability in log responses or variability in continuous measurements, etc.). Discrete measurements may be collected from the selected core samples based on the variability of the continuous measurements. In this example, the analysis will better characterize the core section's geologic and petrologic properties. For example, if an analysis reveals that the core section is homogenous (or substantially homogeneous), then there may be no need to obtain additional samples. However, if the analysis reveals that the core section is not homogeneous (or substantially heterogeneous), then additional samples from within the core section may be obtained for analysis, to determine the extent of heterogeneity within the core section and properties associated with each of the heterogeneous sections within the core section.

In one or more embodiments, the analysis of the integrated overlay using continuous measurements may include re-interpreting or confirming geologic interpretations. For example, it may be possible to perform a quantitative analysis of heterogeneity on an integrated overlay to determine locations of selected core samples. In another example, it may be possible to perform a quantitative analysis of heterogeneity on an integrated overlay to determine the massive and bedded sections of a sample. In this example, the sections may then be used to define the selected core samples used for additional testing.

In another embodiment, the quantitative analysis of heterogeneity may be compared with log predictions of strength to determine the locations of the selected core samples. In this example, the higher resolution of the continuous strength measurements may be used to identify low strength areas not identifiable through the log predictions. The low strength areas may indicate that additional analysis should be performed because of an increased risk of sanding. The additional analysis may be performed by obtaining selected core samples from those areas identified by the continuous measurements for additional analysis.

In one or more embodiments, statistical analysis may be used to identify locations within the core from which to obtain selected core samples. An example of statistical analysis that may be used with continuous measurements is ternary diagrams. Ternary diagrams are visualizations that help characterize similarities in the composition of the material by discriminating three dominant groups of minerals (ternary diagrams are not shown). When the three dominant groups of minerals are combined with a contour map of the continuous measurements (e.g., strength), the result may show graphically that many samples with similar composition have similar strength. When many samples with similar composition have similar strength, composition may be the primary control of strength (possibly because the texture is invariant). Alternatively, if samples with the same composition show considerable variability in strength, the considerable variability in strength may suggest that composition alone is not the driver of strength. When considerable variability in strength exists, textural observations (e.g., grain size, shape, and grain size distribution, micro-bedding, or alternate combinations of beds with different grain size that give rise to a laminated texture) may be performed. In one or more embodiments, the textural observations are coded (with colors or numbers) for graphical evaluation. Combining the two observations (texture and composition) in the same ternary diagram provides a visually apparent means to understand how the combinations of composition and texture may result in similar or dissimilar strength. In one or more embodiments, the combination of the two observations may be incorporated into a model that relates the continuous measurements to the geologic and petrologic measurements of texture and composition. Those skilled in the art will appreciate that further testing may be useful to characterize other properties of the core section.

In one or more embodiments, once the analysis described above is completed, the locations to obtain the selected core samples are defined. The selected core samples will provide discrete measurements to more accurately characterize the material properties of an area of interest. Also, if groups of core samples are analyzed for specific material property characterization (e.g., for failure envelope analysis based on five triaxial tests at multiple levels of confinement), then selection of core samples may provide a high certainty that the samples will be representative of each other (i.e., the core samples are properly grouped). The samples are likely to be representative of each other because the selected core samples are defined based on statistical analysis, as described above. The statistical analysis is used to ensure adequate representation of the variability of the core, log, and/or well heterogeneity.

Scaling may be used to relate the core measurements to log responses. Scaling uses cluster units correlated with patterns of log responses to relate with small scale petrologic measurements. Scaling may be performed based on a defined reference scale (e.g., cluster analysis at log resolution). For example, upscaling may be performed from smaller scales to the reference scale, using statistical methods. In another example, downscaling may be performed from larger scales to the reference scale, or from the reference scale to a smaller scale, using pattern recognition or self adapting statistical algorithms. Thus, scaling petrologic data to well log data includes defining cluster units with characteristic combined log responses representing characteristic material properties. For example, high resolution continuous measurements may be used to perform a statistical analysis of the variability of the measured property or properties, along the length of the particular cluster. An output of the statistical evaluations may be the box-and-whisker plot representation, where the box is defined by a mean value and the upper and lower quartiles of the data (two standard deviations). The whiskers include the rest of the data. Thus, distributions with short boxes represent almost constant values, and distributions with long boxes represent large variability in the measured data. After the cluster analysis is conducted along the core section, the clusters, as they relate to the variability of log responses, are applied to other sections of the log. Applying the clusters to other sections of the log is referred to as cluster tagging, described in more detail below. The compliance between the combined log responses and the other sections of the log are quantified by an error function to determine locations of low compliance. The locations of low compliance are not represented by materials sampled in the core section.

A method of performing scaling with geological measurements may use the descriptive (non quantitative) nature of geology, and as such is different than the quantitative analysis described above. However, when provided with the continuous measurements and the overlay of continuous measurements and digital core photography, geologists may be more specific and consistent in their descriptions and the descriptions therefore become more quantifiable. For example, a coarsening upward sequence due to the observation of the gradual increase in grain size in a rock section indicates a measurable trend of increasing strength, where one can measure the upper and lower values and the length of the sequence using the continuous measurements overlaid with the digital core photography.

In one or more embodiments, statistical models are developed based on the statistical analysis. In one or more embodiments, the statistical models are developed on a per-cluster basis using the continuous measurements, the analysis of the integrated overlay data, and the discrete measurements obtained from the sample analysis. The output data of the statistical model for each of the clusters is analyzed to create statistical distributions of the measurements in order to characterize representative variability of the measured properties and the log responses defining the individual cluster units.

Using the statistical distributions, models are created that predict values of each measured property along the entire logged section, which includes the cored section, to obtain a set of predicted values for the material along the length of the logged section.

In one or more embodiments, the statistical models may be used to conduct predictions or to solve field problems. In one or more embodiments, the predicted values from models are compared with results from discrete measurements. The predicted values may also be compared with results of continuous measurements, when possible. The data from the comparison of the predicted values with the results of the continuous measurements is used with cluster tagging methodology to assign an index of reliability to the predicted values. The index of reliability identifies clusters outside the core that are identical to clusters existing in the core and such clusters are given high compliance ratings. Conversely, the clusters outside the core that do not compare well with clusters existing in the core are given low compliance ratings. Therefore, predictions with high reliability correspond to cluster units with high compliance ratings.

In the case where a core section was obtained from a well and, after laboratory testing, statistical models relating core data to log data were obtained, statistical models may be used to conduct predictions on subsequent adjacent wells using logs from the adjacent wells. In this example, the adjacent well logs may be analyzed using the cluster analyzes discussed above using the log definitions for clusters identified in the reference well (i.e., the well from which the core section measurements were obtained and analyzed). The results of the cluster analysis may then be used along with an analysis of predicted values for properties to obtain predictions of the material property of the adjacent well based on the previously developed model.

Those skilled in the art will appreciate that continuous measurement of geomaterials may integrate methods of cluster analysis and cluster tagging used for defining heterogeneity at a log-scale with methods to provide quantitative assessments of heterogeneity of material properties at a core-scale. In this example, the continuous measurements and profiles of material properties obtained on core or rock samples are related to continuous measurements and profiles (i.e., well logs) obtained from wells. Integrating heterogeneity at a log-scale and heterogeneity of material properties at a core-scale via cluster analysis allows for better selection of well locations for coring, core sections or side wall plugs, and better sampling and characterization of cluster units. In addition integrating heterogeneity at a log-scale and heterogeneity of material properties at a core-scale via cluster analysis results in more accurate development of models between cluster units (defined at log resolution), and measured continuous and discrete material properties.

In one or more embodiments, cluster analysis may be performed on continuous measurements. The cluster analysis may correspond to a statistical multidimensional analysis that partitions data into subsets, each of which share a common trait. In other words, the results of the continuous measurements are partitioned into groups where the results in each group share a common trait or set of measurements. In particular, cluster analysis may identify rock units with similar and dissimilar combined log responses. The rock units with similar combined log responses are then defined as clusters. The results of cluster analysis may represent clusters using colors, where similar colors identify areas with similar material properties. Cluster analysis is beneficial because cluster analysis sets a common reference for evaluation of material properties by many disciplines, including but not limited to geology, petrology, geophysics, and laboratory characterization. Cluster analysis is also beneficial because cluster analysis may show heterogeneity at log scale or sub-log scale, cluster analysis discriminates areas of consistent clay behavior within a heterogeneous area, and models calibrated using a core at the cluster level may be more robust.

In one or more embodiments, cluster analysis may be used in combination with an analysis of integrated overlays to select locations in a geomaterial or core section. More specifically, the selection of locations within the geomaterial or core section may be performed based on the cluster analysis, analysis of variability in log responses within each cluster, analysis of variability of many continuous measurements conducted on the core section, and/or visual variability of core texture. The cluster analysis may also be analyzed to determine proper sampling required to adequately represent each cluster.

Example of Automated Sampling

Consider an example of a process for automated sampling, as described above. Initially, the results of a cluster analysis are obtained. Then, the clusters within the interval where the core exists are evaluated, as are the top and bottom core depths associated to the boundaries of each cluster. Next, outliers of the cluster data are removed. When outliers of the cluster data are removed, the ratio of the combined length of the cluster units with the same color (i.e., cluster group) to the total length of the core is calculated. In addition, a second ratio is calculated by dividing the length of the core equally by the number of clusters. Then, the degree of dominance of each cluster group is evaluated using the two ratios previously calculated. The most dominant clusters and the standard clusters may receive a sampling redundancy (i.e., the degree of replication) of 2, and the least dominant clusters may receive a sampling redundancy of 0.5.

Next, after saving the results of the high resolution continuous measurements on the core section, the statistical frequency distributions of each of the high resolution continuous measurements on the core section is calculated on a cluster-by-cluster basis. Then, the individual statistical distribution for each of the individual clusters of the same designation is compared to the combined variability for other sections with the same cluster designation. Next, if the statistical distributions of clusters of the same designation located in different sections of the core result in bi-modal or-tri-modal distributions, a warning for re-clustering is triggered. When multiple continuous measurements on the core sample are performed and evaluated, they are given a weighting factor (as manually assigned or as determined based on internal experience associated to previous completed projects) of their importance in the analysis. Optionally, a box-and-whisker plot of the combined statistical distributions for each cluster color may be presented.

Continuing with the example, the variability between the median value of the entire distribution and the median value of the first and third quartile of the distribution (which corresponds to the percent variability between the median value and the edges of the box plot) is calculated. Then, the variability between the median value of the first and third quartile of the distribution and the maximum and minimum values of the distribution (which corresponds to the percent variability between the edges of the box plot and the whiskers of the distribution) is calculated. When the variability between the median value of the first and third quartile of the distribution and the maximum and minimum values of the distribution is calculated, sampling coefficient factors defined based on previous experience are compared with corresponding threshold values for each of the two prior calculations, and the results are added to obtain the final number of samples per cluster. Next, the number of samples needed per cluster are consolidated, and the sampling redundancy coefficient (described above) is applied to determine the total number of samples needed per cluster designation. Then, other corresponding locations in the core associated to the desired property values for each cluster are selected.

Still continuing with the example, other possible locations for the desired values to the log responses are compared based on criteria such as minimum hole enlargement, best quality log data, and minimum variability in the log data to within some distance of a selected point. The candidate points not meeting the criteria may be eliminated. Next, the remaining points are compared with the continuous measurements of the core sample, and those that exist in a range of stable values within a defined distance of the selected point are retained. The remaining points are considered high quality and are presented as highlighted on a cluster by cluster level. Then, final locations for sampling are recorded in a sample selection log and overlaid to plots displaying logs, core images, and continuous measurements. Next, samples along each of the desired locations are obtained. When drilling samples, measurements of torque, weight on bit, and depth of penetration of the sample to the coring barrel are used to identify sample quality. If the sample quality is acceptable, the operation continues to the next location. If the sample quality is rejected, the best equivalent sample from the list is chosen. Once the samples are obtained as desired, the operation is completed.

The apparatus for continuous measurement of geomaterials may be connected to a computer system running a software program to conduct the aforementioned analysis to determine the relationship between the log responses and selected core section, to obtain the continuous measurements, to create the overlays of continuous measurements with log responses, integrate the overlays with geologic/petrologic observations and descriptions, and analyze the integrated overlays to determine selected core samples. The samples may be obtained by the apparatus in an automated fashion, in which case the apparatus may perform an initial pass of the core section to perform the continuous measurements and then perform a second pass of the core section to plug identified core sections and/or core samples. Also, while plugging, the apparatus may perform additional measurements of torque, rate of penetration, etc. The additional measurements may be used for subsequent comparison and analysis, and to identify sample quality.

Figure 10:
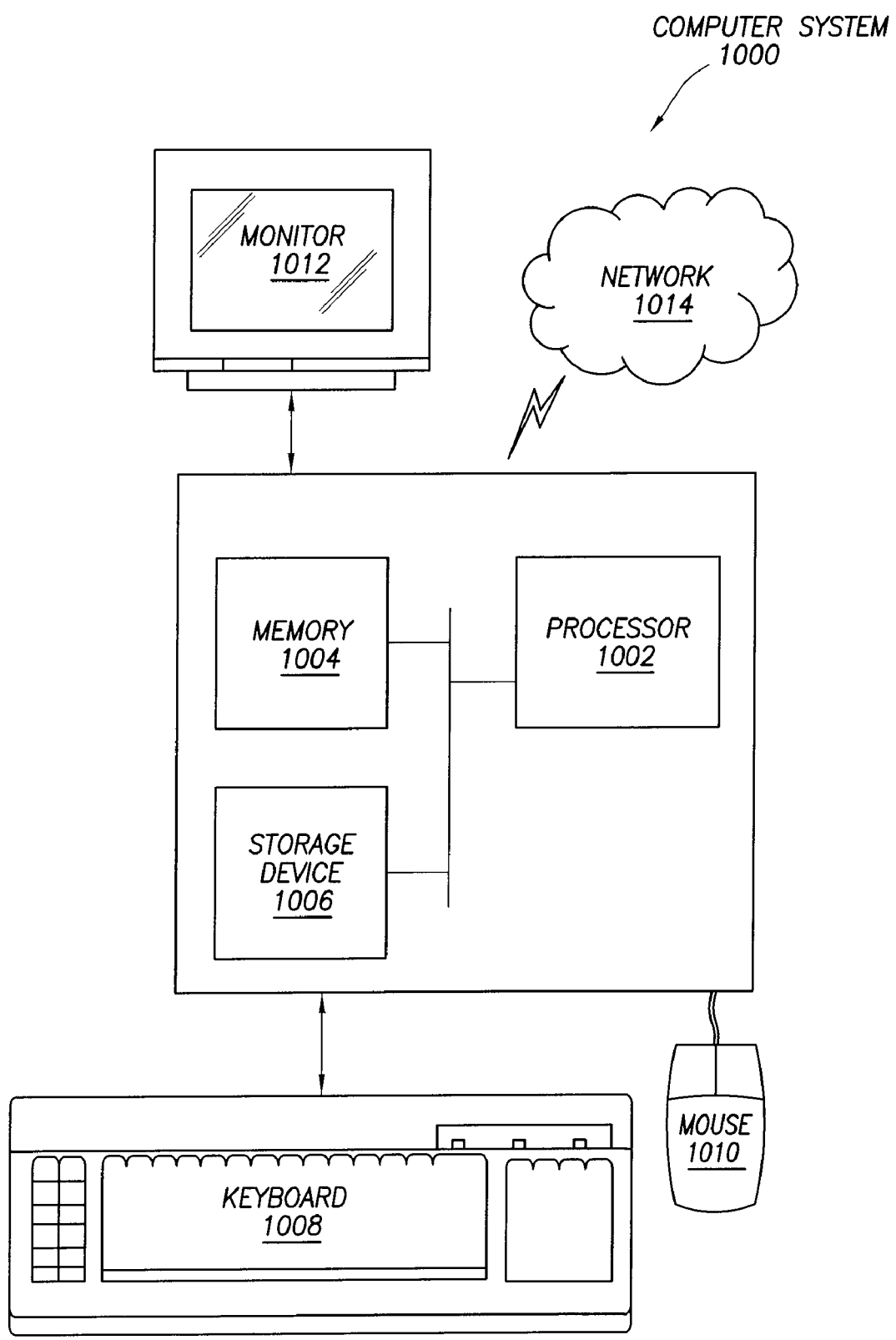
FIG. 10 illustrates a computer system in which one or more embodiments of a continuous measurement of geomaterials may be implemented.

Embodiments may be implemented on virtually any type of computer regardless of the platform being used. For example, as shown in FIG. 10, a computer system (1000) includes one or more processor(s) (1002), associated memory (1004) (e.g., random access memory (RAM), cache memory, flash memory, etc.), a storage device (1006) (e.g., a hard disk, an optical drive such as a compact disk drive or digital video disk (DVD) drive, a flash memory stick, etc.), and numerous other elements and functionalities typical of today's computers (not shown). The computer (1000) may also include input means, such as a keyboard (1008), a mouse (1010), or a microphone (not shown). Further, the computer (1000) may include output means, such as a monitor (1012) (e.g., a liquid crystal display (LCD), a plasma display, or cathode ray tube (CRT) monitor). The computer system (1000) may be connected to a network (1014) (e.g., a local area network (LAN), a wide area network (WAN) such as the Internet, or any other similar type of network) via a network interface connection (not shown). Those skilled in the art will appreciate that many different types of computer systems exist, and the aforementioned input and output means may take other forms, now known or later developed. Generally speaking, the computer system (1000) includes at least the minimal processing, input, and/or output means necessary to practice embodiments of continuous measurement of geomaterials.

Further, those skilled in the art will appreciate that one or more elements of the aforementioned computer system (1000) may be located at a remote location and connected to the other elements over a network. Further, embodiments of continuous measurement of geomaterials may be implemented on a distributed system having a plurality of nodes, where each portion of the embodiments may be located on a different node within the distributed system. In one or more embodiments, the node corresponds to a computer system. Alternatively, the node may correspond to a processor with associated physical memory. The node may alternatively correspond to a processor with shared memory and/or resources. Further, software instructions to perform embodiments of continuous measurement of geomaterials may be stored on a computer readable medium such as a compact disc (CD), a diskette, a tape, or any other computer readable storage device.

While continuous measurement of geomaterials has been described with respect to a limited number of embodiments, those skilled in the art, having benefit of this disclosure, will appreciate that other embodiments can be devised which do not depart from the scope of continuous measurement of geomaterials as disclosed herein. Accordingly, the scope of continuous measurement of geomaterials should be limited only by the attached claims.

What is claimed is:

1. An apparatus for continuous measurement of a geomaterial, comprising:
 a measuring device comprising:
  a moving head configured to move in a longitudinal direction relative to a core section of the geomaterial; and
  a first probe coupled to the moving head and configured to continuously measure a first property of the core section;
  a second probe coupled to the moving head and configured to continuously measure a second property associated with the core section, wherein the measured first property and the measured second property are combinable to generate an overlay; and
 a flat bed operatively coupled to the measuring device and comprising:
  a load actuator configured to:
   secure the core section during the continuous measurement; and
   axially rotate the core section; and
  a core holder assembly configured to apply confining pressure on a length of the core section, wherein the confining pressure is at least partially circumferential.

2. The apparatus of claim 1, further comprising:
 a controller configured to adjust a depth of the first probe during the continuous measurement.

3. The apparatus of claim 1, wherein the first probe is configured to continuously measure a hardness of the geomaterial by applying pressure to the surface of the geomaterial.

4. The apparatus of claim 1, wherein the core holder assembly applies confining pressure along the length of the core section using a curved platen during the continuous measurement.

5. The apparatus of claim 1, wherein the second probe is configured to obtain a plurality of visual representations along the core section as the first probe continuously measures the property of the core section, and wherein each of the plurality of visual representations is overlaid with the continuous measurement of the property for a corresponding portion of the core section.

6. The apparatus of claim 1, wherein the first probe emits a series of frequencies during the continuous measurement, and wherein the second probe is configured to measure the series of frequencies.

7. The apparatus of claim 1, wherein the first probe is configured to emit an energy wave directed at a first location of the core section, and wherein the second probe is configured to continuously measure the energy wave at a second location of the core section.

8. The apparatus of claim 1, the measuring device configured to:
 perform a first continuous strength measurement on the core section using the first probe to generate a first result, wherein the first result is generated prior to immersing the core section in a fluid for a period of time;
 after the core section is immersed in the fluid for the period of time, perform a plurality of continuous strength measurements at incrementally increasing depths of the core section using the first probe, each of the plurality of continuous strength measurements generating a corresponding result of a plurality of results; and
 determine an invasion zone of the fluid as the depth of the first probe during one of the plurality of continuous strength measurements, wherein the corresponding result associated with the one of the plurality of continuous strength measurements is substantially the same as the first result.

9. The apparatus of claim 1, wherein at least the moving head, the load actuator, the core holder assembly, and the first probe are stiffly connected.

10. The apparatus of claim 1, wherein the load actuator is further configured to:
 apply axial stress to the core section during the continuous measurement.

11. The apparatus of claim 1, wherein the first probe comprises a light source and an optical receiver, wherein the light source emits a light toward the core section, and wherein the optical receiver measures the light reflected off the core section.

12. An apparatus for continuous measurement of a geomaterial comprising:
 a measuring device comprising:
  a moving head configured to move in a longitudinal direction relative to a core section of the geomaterial;
  a first probe coupled to the moving, head and configured to continuously measure a first property of the core section, wherein the first probe comprises an abrasive material; and
  a second probe coupled to the moving head and configured to continuously measure a second property associated with the core section, wherein the measured first property and the measured second property are combinable to generate an overlay, and wherein the second probe is further configured to continuously measure a load on the first probe to determine a wear of the abrasive material as the first probe scratches a surface of the core section; and
 a flat bed operatively coupled to the measuring device and comprising:
  a load actuator configured to:
   secure the core section during the continuous measurement; and
   axially rotate the core section; and a core holder assembly configured to apply confining pressure on a length of the core section.

13. An apparatus for continuous measurement of a geomaterial, comprising:
a measuring device comprising:
a moving head configured to move in a longitudinal direction relative to a core section of the geomaterial;
a first probe coupled to the moving head and configured to continuously measure a first property of the core section, wherein the first probe comprises:
a spray device configured to emit an atomized fluid on the core section at a location; and
a measuring tool configured to continuously measure the first property of the core section at the location; and
a second probe coupled to the moving head and configured to continuously measure a second property associated with the core section, wherein the measured first property and the measured second property are combinable to generate an overlay; and
a flat bed operatively coupled to the measuring device and comprising:
a load actuator configured to:
secure the core section during the continuous measurement; and
axially rotate the core section; and
a core holder assembly configured to apply confining pressure on a length of the core section.

14. An apparatus for continuous measurement of a geomaterial, comprising:
a measuring device comprising:
a moving head configured to move in a longitudinal direction relative to a core section of the geomaterial;
a first probe coupled to the moving head and configured to continuously measure a first property of the core section, wherein the first probe comprises a vacuum in which the first property is measured; and
a second probe coupled to the moving head and configured to continuously measure a second property associated with the core section; wherein the measured first property and the measured second property are combinable to generate an overlay; and
a flat bed operatively coupled to the measuring device and comprising:
a load actuator configured to:
secure the core section during the continuous measurement; and
axially rotate the core section; and
a core holder assembly configured to apply confining pressure length of the core section.

15. An apparatus for continuous measurement of a geomaterial, comprising:
a measuring device comprising:
a moving head configured to move in a longitudinal direction relative to a core section of the geomaterial;
a first probe coupled to the moving head and configured to continuously measure a first property of the core section; and
a second probe coupled to the moving head and configured to continuously measure a second property associated with the core section, wherein the measured first property and the measured second property are combinable to generate an overlay;
a flat bed operatively coupled to the measuring device and comprising:
a load actuator configured to:
secure the core section during the continuous measurement; and
axially rotate the core section; and
a core holder assembly configured to apply confining pressure on a length of the core section; and
a pressure cell configured to apply a controlled environment to the core section.

16. An apparatus for continuous measurement of a geomaterial, comprising:
a measuring device comprising:
a moving head configured to move in a longitudinal direction relative to a core section of the geomaterial;
a first probe coupled to the moving head and configured to continuously measure a first property of the core section in a first continuous measurement; and
a second probe coupled to the moving head and configured to extract a plurality of core samples from the core section;
a flat bed operatively coupled to the measuring device and comprising:
a load actuator configured to:
apply axial stress to the core section; and
axially rotate the core section; and
a core holder assembly configured to apply confining pressure on the length of the core section; and
a controller configured to determine, based on the first continuous measurement, a location to extract each of the plurality of core samples from the core section.

17. The apparatus of claim 16, wherein the first probe is further configured to continuously measure the first property of each of the plurality of core samples in a second continuous measurement.

18. The apparatus of claim 16, wherein the second probe is further configured to measure a second property of each of the plurality of core samples while extracting the plurality of core samples.

19. The apparatus of claim 16, wherein determining the location on the core section to extract each of the plurality of core samples comprises:
receiving a log response associated with the core section;
generating an overlay using the first continuous measurement and the log response;
receiving geologic observations and petrologic observations corresponding to the core section;
integrating the overlay with the geologic observations and petrologic observations to generate an integrated overlay of the core section; and
determining the location on the core section to extract each of the plurality of core samples based on the integrated overlay.

* * * * *